United States Patent [19]

Jean-Louis et al.

[11] Patent Number: 4,833,154

[45] Date of Patent: May 23, 1989

[54] NATURAL SLEEPING PILL TO PREVENT AND ALLEVIATE INSOMNIA

[76] Inventors: Louis J. Jean-Louis; Sylvia L. Jean-Louis, both of 951 mWillowleaf Dr., No. 1404, San Jose, Calif. 95128

[21] Appl. No.: 132,327

[22] Filed: Dec. 14, 1987

[51] Int. Cl.⁴ ........................ A61U 31/34; A61U 31/40
[52] U.S. Cl. ..................................... 514/419; 514/474
[58] Field of Search ................................ 514/419, 474

[56] References Cited

U.S. PATENT DOCUMENTS 4,596,807  6/1986  Crosby ................................ 514/474

*Primary Examiner*—Stanley J. Friedman
*Attorney, Agent, or Firm*—Michael J. Hughes

[57] ABSTRACT

A natural sleeping pill for preventing and alleviating insomnia, designed specifically for people who enjoy absolutely no benefit from other conventional drugs and those who abstain from their use because of their highly addictive nature and side-effects and the same comprises Vitamin C in dosage, including but not limited to, 10,000 MG; L-Tryptrophane in dosage, including but not limited to, 6,000 MG; Calcium in dosage, including but not limited to, 1,000 MG; and Inositol in dosage, including but not limited, to 1,000 MG. The foregoing dosages may be increased or decreased to suit the particular needs of the different facets of the insomniac population. Moreover, the different dosages of these four (4) natural and organic substances will be pulverized and may be recommended for use as is or enclosed in a bio-degradable capsule for oral ingestion by those seeking genuine relief from insomnia. This is, in short, the formula for a revolutionary, highly efficient, non-addictive, natural sedative to prevent, treat otherwise alleviate insomnia, thereby bring genuine relief to tens of millions of people who are suffering from this so-called incurable disease.

5 Claims, No Drawings

NATURAL SLEEPING PILL TO PREVENT AND ALLEVIATE INSOMNIA

BACKGROUND—FIELD OF INVENTION

This invention relates to the field of natural, non-prescription sleeping medications. It's a natural sedative which prevents and alleviates insomnia. It is specifically designed for all people, especially those who, for one reason or another, do not find any relief from the use of other conventional drugs. Some of these people are reluctanct to ingest these products because of their highly addictive nature and the dangerous side-effects they cause.

BACKGROUND—DESCRIPTION OF PREVIOUS ART

Most, if not all, consumers prefer a natural sleeping pill which is non-addictive, highly effective with minimal or no side-effects.

Heretofore a wide variety of sleeping medications have been produced and are currently available on the market today. Each one of them, however, has some rather serious drawbacks. Some of them provide relief only to a small segment of the insomniac population, while the majority of those suffering from this terrible disease derive no benefit from them whatsoever. Others are highly addictive and produce some dangerous side-effects. These side-effects range from drowsiness to dry mouth, dizziness, blurred vision, stuffy nose, constipation, rapid heart beat, muscle spasms, restlessness, stiffness, uncontrollable trembling and shaking of hands, fingers and feet, reduced sexual drive, infertility, major weight gain and menstrual irregularities in women. In addition, the possibility still exists that the protracted use of these prescriptions may later cause other physical and emotional problems that are yet unknown to the medical community. It is not hyperbolic, then, to corroborate that the risks that some of these sleeping pills pose to consumers' health and physical wellbeing far outweigh the temporary relief they derive from their use. It is, therefore, conclusive that the tens of millions of people who are suffering from insomnia will find it highly desirable to have a sleeping pill, which is highly effective, non-addictive and does not cause any of the foregoing side-effects.

OBJECTS AND ADVANTAGES

Consequently, we claim the following as the objects and advantages of the invention: to produce a highly effective and natural sleeping pill to prevent and relieve insomnia. This substance is specifically designed for all people, especially those who find that other conventional medications that are currently on the market do not alleviate their condition.

In addition, we claim the following objects and advantages: to formulate a substance which seems to work 100% of the time; to produce a substance which is *NOT* addictive; to invent a natural sedative that has no apparent side-effects for the sole purpose of helping people who are suffering from severe, not-so-severe and mild cases of insomnia. Additional and further objects and advantages of the invention will become more apparent once this product is manufactured on a commercial basis and made available to the tens of millions in this country and around the world who are presently suffering from this terrible sleeping disorder. This will give them the opportunity to choose between hard-core sleeping pills, which are known to be highly habit-forming and cause serious side-effects, and a natural substance, which poses no threat or danger to their physical health and well-being.

DESCRIPTION OF INVENTION

This natural sleeping pill will be formulated by combining:

1. Vitamin C in dosage between 50 and 10,000 MG.
2. Inositol in dosages between 50 and 10,000 MG.
3. L-Tryptrophane in dosages between 500 and 10,000 MG.
4. Calcium in dosages between 200 and 6,000 MG.

The dosage will be employed according to the intensity of the disease. For instance, for severe cases of insomnia, the following dosages will be used:
  L-Tryptrophane: 2,500 MG.
  Calcium: 1,000 MG.
  Vitamin C: 1,000 MG.
  Inositol: 800 MG.

For not-so-severe cases of insomnia, the dosage to be utilized is as follows:
  L-Tryptrophane: 1,000 MG.
  Vitamin C: 500 MG.
  Calcium: 500 MG.
  Inositol: 400 MG.

For mild cases, the following dosage will be recommended:
  L-Tryptrophane: 1,200 MG.
  Calcium: 200 MG.
  Vitamin C: 100 MG.
  Inositol: 50 MG.

OPERATION OF INVENTION

This combination of four (4) natural subsances will be pulverized, throughly mixed, encapsulated and recommended to be ingested orally to induce sleep. This product will be of great benefit to those who are reluctant to use conventional sleeping medications that are on the market because of health, moral or spiritual reasons. It will further provide them with an alternative to those medications that are highly habit-forming and cause a very high incidence of chemical dependency.

CONCLUSION AND SCOPE OF INVENTION

While our aforementioned description contains many features and specificities that are unique indeed, the reader should not construe these as limitations on the scope of the invention, but merely as an exemplification of one preferred embodiment thereof. Many other variations of this same formula are possible. For instance, the minimum dosage of each substance may be decreased, and the maximum likewise increased, to reflect the strength deemed most appropriate to suit each segment of the insomniac population, depending on the severity of their illness. Accordingly, the reader is requested to determine the scope of the invention by the appended claim and its legal equivalents, and not solely by the particular examples which have been given. The reader should further note that, while most of the commonly-used sleeping pills, which are produced for commercially, are highly addictive and cause some serious, if not dangerous, side-effects—this sleeping pill is 100% natural. It is non-addictive. It causes no apparent side-effects. And, last not least, it seems to induce sleep 100% of the time according to testimonials from those who have used it. Therefore, it will be widely accepted by the tens of millions of victims all over the world who are looking for a sound and safe way to overcome this annoying disease, call insomnia.

We claim:

1. A natural and nonaddictive sleeping potion composition for preventing and treating insomnia, the ingredients comprising:

vitamin C in dosage of between 50 mg and 10,000 mg;

L-tryptophane in dosage of between 500 mg and 10,000 mg;

calcium in dosage of between 200 mg and 6,00 mg; and inositol in dosage of between 50 mg and 10,000;

wherein the ingredients are mixed together in powdered form to form a substantially homogeneous powder for oral ingestion.

2. The sleeping potion composition of claim 1 wherein
said dosage of vitamin C is about 1500 mg;
said dosage of L-tryptophane is about 2500 mg;
said doasge of calcium is about 1500 mg; and
said dosage of inositol is about 800 mg.

3. The sleeping potion composition of claim 1 wherein
said dosage of Vitamin C is about 700 mg;
said dosage of L-tryptophane is about 1500 mg;
said dosage of calcium is about 750 mg; and
said dosage of inositol is about 400 mg.

4. The sleeping potion composition of claim 1 wherein:
said dosage of Vitamin C is about 500 mg;
said dosage of L-tryptophane is about 1000 mg;
said dosage of calcium is about 300 mg; and
said dosage of inositol is about 200 mg.

5. The sleeping potion composition of claim 1 wherein
said ingredients are pulverized, thoroughly mixed and placed into capsules for easy ingestion.

* * * * *